US00PP30962P2

(12) United States Plant Patent
Matsumoto

(10) Patent No.: US PP30,962 P2
(45) Date of Patent: Oct. 22, 2019

(54) ***VERBENA* PLANT NAMED 'RIKAV44101'**

(50) Latin Name: *Verbena hybrida*
Varietal Denomination: RIKAV44101

(71) Applicant: Rika Matsumoto, Omihachiman (JP)

(72) Inventor: Rika Matsumoto, Omihachiman (JP)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 15/998,155

(22) Filed: Jul. 10, 2018

(51) Int. Cl.
*A01H 5/02* (2018.01)
*A01H 6/86* (2018.01)

(52) U.S. Cl.
USPC ..... Plt./308
CPC ..... *A01H 6/86* (2018.05)

(58) Field of Classification Search
USPC ..... Plt./308
CPC ..... A01H 6/86; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Verbena* plant named 'RIKAV44101', characterized by its outwardly spreading to mounding plant habit; vigorous growth habit; freely branching habit; dark green-colored leaves; freely flowering habit; relatively large dark red-colored flowers that are held above and beyond the foliar plane; and relative tolerance to Powdery Mildew (*Podosphaera xanthii*).

1 Drawing Sheet

Botanical designation: *Verbena hybrida.*
Cultivar denomination: 'RIKAV44101'.

BACKGROUND OF THE INVENTION

The present invention relates to a new and distinct cultivar of *Verbena* plant, botanically known as *Verbena hybrida*, and hereinafter referred to by the name 'RIKAV44101'.

The new *Verbena* plant is a product of a planned breeding program conducted by the Inventor in Higashiomi, Shiga, Japan and Bonsall, Calif. The objective of the breeding program is to create new vigorous and freely-branching *Verbena* plants with numerous flowers and tolerance to Powdery Mildew (*Podosphaera xanthii*).

The new *Verbena* plant originated from a cross-pollination made by the Inventor on May 18, 2015 in Higashiomi, Shiga, Japan of a proprietary seedling selection of *Verbena hybrida* identified as code number 13V349-02, not patented, as the female, or seed, parent with a proprietary seedling selection of *Verbena hybrida* identified as code number 13V308-02, not patented, as the male, or pollen, parent. The new *Verbena* plant was discovered and selected by the Inventor as a single flowering plant from within the progeny of the stated cross-pollination in a controlled greenhouse environment in Bonsall, Calif. on May 26, 2016.

Asexual reproduction of the new *Verbena* plant by vegetative terminal cuttings in a controlled environment in Bonsall, Calif. since May 30, 2016, has shown that the unique features of this new *Verbena* plant are stable and reproduced true to type in successive generations.

SUMMARY OF THE INVENTION

Plants of the new *Verbena* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'RIKAV44101'. These characteristics in combination distinguish 'RIKAV44101' as a new and distinct *Verbena* plant:

1. Outwardly spreading to mounding plant habit.
2. Vigorous growth habit.
3. Freely branching habit.
4. Dark green-colored leaves.
5. Freely flowering habit.
6. Relatively large dark red-colored flowers that are held above and beyond the foliar plane.
7. Relatively tolerant to Powdery Mildew (*Podosphaera xanthii*).

Plants of the new *Verbena* can be compared to plants of the female parent selection. Plants of the new *Verbena* differ primarily from plants of the female parent selection in the following characteristics:

1. Plants of the new *Verbena* are more spreading than and not as mounding as plants of the female parent selection.
2. Plants of the new *Verbena* are more vigorous than plants of the female parent selection.
3. Plants of the new *Verbena* have larger flowers than plants of the female parent selection.
4. Plants of the new *Verbena* are more tolerant to Powdery Mildew than plants of the female parent selection.

Plants of the new *Verbena* can be compared to plants of the male parent selection. Plants of the new *Verbena* differ primarily from plants of the male parent selection in the following characteristics:

1. Plants of the new *Verbena* are more vigorous than plants of the male parent selection.
2. Plants of the new *Verbena* are more freely branching than plants of the male parent selection.

3. Plants of the new *Verbena* flower more continuously than plants of the male parent selection.
4. Plants of the new *Verbena* and the male parent selection differ in flower color as plants of the male parent selection have darker red-colored flowers with white-colored "eyes".

Plants of the new *Verbena* can be compared to plants of the *Verbena hybrida* 'Lan Reda07', disclosed in U.S. Plant Pat. No. 18,986. In side-by-side comparisons, plants of the new *Verbena* differ primarily from plants of 'Lan Reda07' in the following characteristics:

1. Plants of the new *Verbena* are more vigorous than plants of 'Lan Reda07'.
2. Plants of the new *Verbena* have larger flowers than plants of 'Lan Reda07'.
3. Plants of the new *Verbena* are more tolerant to Powdery Mildew than plants of 'Lan Reda07'.

Plants of the new *Verbena* can be compared to plants of the *Verbena hybrida* 'Usbenal5', disclosed in U.S. Plant Pat. No. 14,851. In side-by-side comparisons, plants of the new *Verbena* differ primarily from plants of 'Usbenal5' in the following characteristics:

1. Plants of the new *Verbena* are more mounding than and not as upright as plants of 'Usbenal5'.
2. Plants of the new *Verbena* and 'Usbenal5' differ in flower color as plants of 'Usbenal5' have purple-colored flowers.
3. Plants of the new *Verbena* are more tolerant to Powdery Mildew than plants of 'Usbenal5'.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the actual colors of the new *Verbena* plant.

The photograph at the bottom of the sheet comprises a side perspective view of a typical flowering plant of 'RIKAV44101' grown in a container.

The photograph at the top of the sheet is a close-up view of a typical flowering plant of 'RIKAV44101'.

DETAILED BOTANICAL DESCRIPTION

The aforementioned photographs and following observations and measurements describe plants grown during the spring in 10-cm containers in an acrylic-covered greenhouse in Carleton, Mich. and under cultural practices typical of commercial *Verbena* production. During the production of the plants, day and night temperatures ranged from 18° C. to 24° C. Plants were twelve weeks old when the photographs and description were taken. In the following description, color references are made to The Royal Horticultural Society Colour Chart, 2007 Edition, except where general terms of ordinary dictionary significance are used.

Botanical classification: *Verbena hybrida* 'RIKAV44101'.

Parentage:

*Female, or seed, parent*.—Proprietary seedling selection of *Verbena hybrida* identified as code number 13V349-02, not patented.

*Male, or pollen, parent*.—Proprietary seedling selection of *Verbena hybrida* identified as code number 13V308-02, not patented.

Propagation:

*Type cutting*.—Vegetative terminal cuttings.

*Time to initiate roots, summer*.—About three days at temperatures ranging from about 16° C. to 29° C.

*Time to initiate roots, winter*.—About four days at temperatures ranging from about 16° C. to 21° C.

*Time to produce a rooted plant, summer*.—About 15 days at temperatures ranging from about 16° C. to 29° C.

*Time to produce a rooted plant, winter*.—About 20 days at temperatures ranging from about 16° C. to 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Outwardly spreading to mounding plant habit; freely branching habit with about seven primary lateral branches each with about six to eight secondary lateral branches developing per plant; pinching is not required; dense and bushy plant habit; vigorous growth habit.

*Plant height, soil level to top of foliar plane*.—About 10 cm.

*Plant height, soil level to top of floral plane*.—About 12.5 cm.

*Plant diameter (spread)*.—About 27 cm by 30 cm.

Lateral branch description:

*Length*.—Variable, about 12.5 cm.

*Diameter*.—About 2 mm.

*Internode length*.—About 3.3 cm.

*Orientation*.—Initially upright then outwardly spreading to trailing.

*Strength*.—Strong.

*Texture and luster*.—Pubescent; matte.

*Color, developing*.—Close to 146B.

*Color, developed*.—Close to 146A.

Leaf description:

*Arrangement*.—Opposite, simple.

*Length*.—About 4 cm.

*Width*.—About 3.7 cm.

*Shape*.—Deltoid.

*Apex*.—Broadly acute.

*Base*.—Truncate.

*Margin*.—Crenate.

*Texture and luster, upper and lower surfaces*.—Hirsute; matte.

*Venation pattern*.—Pinnate; reticulate.

*Color*.—Developing leaves, upper and lower surfaces: Close to 146B. Fully expanded leaves, upper surface: Close to N137A; venation, close to 147B. Fully expanded leaves, lower surface: Close to 147B; venation, close to 147D.

*Petioles*.—Length: About 5 mm. Diameter: About 2.5 mm. Strength: Moderately strong. Texture and luster, upper and lower surfaces: Pubescent, minute; matte. Color, upper surface: Close to 147C. Color, lower surface: Close to 147C to 147D.

Flower description:

*Flower arrangement and habit*.—Sessile salverform flowers arranged in upright hemispherical terminal racemes; flowers face upward or outwardly; freely flowering habit with about 34 flowers developing per inflorescence and typically more than 700 flowers developing per plant.

*Natural flowering season*.—Plants flower continuously from spring until frost in Michigan; early flowering habit, plants begin flowering about seven weeks after planting.

*Flower longevity*.—Flowers last about five to seven days on the plant; flowers not persistent.

*Fragrance*.—None detected.

*Inflorescence height*.—About 4.4 cm.

*Inflorescence diameter*.—About 6.5 cm.

*Flower buds*.—Length: About 2.1 cm. Diameter: About 4 mm. Shape: Elongated oblong. Texture and luster: Pubescent, minute; matte. Color: Close to 53A.

*Flower diameter*.—About 2.1 cm.

*Flower depth* (*height*).—About 2.8 cm.

*Throat diameter*.—About 1.5 mm.

*Tube length*.—About 2.3 cm.

*Tube diameter, distally*.—About 2 mm.

*Corolla*.—Arrangement: Single whorl of five fused petals fused towards the base into a slender narrow tube. Petal lobe length: About 1.1 cm. Petal lobe width: About 1 cm. Petal lobe shape: Roughly cordate. Petal lobe apex: Emarginate. Petal margin: Entire. Petal texture and luster, upper surface: Smooth, glabrous; matte. Petal texture and luster, lower surface: Pubescent, minute; matte. Throat texture and luster: Pubescent; matte. Tube texture and luster: Scattered pubescence, minute; matte. Color: Petal, when opening, upper and lower surfaces: Close to 53A. Petal, fully opened, upper surface: Close to 46A to 46B; towards the throat, close to 46A; venation, close to 46B; color does not change with development. Petal, fully opened, lower surface: Close to 53C; venation, close to 53C; color does not change with development. Throat: Close to 145D; venation, close to 145D. Tube: Close to 157A; venation, close to 157A.

*Calyx*.—Arrangement: Single whorl of five fused sepals fused towards the base into a slender tube. Length: About 1.1 cm. Diameter: About 2 mm. Sepal length: About 8 mm. Sepal width: Less than 1 mm. Sepal shape: Narrowly lanceolate. Sepal apex: Acute. Sepal margin: Entire. Sepal texture and luster, inner surface: Smooth, glabrous; slightly glossy. Sepal texture and luster, outer surface: Pubescence, minute; matte. Sepal color, when opening and fully opened, upper surface: Close to 145B. Sepal color, when opening and fully opened, lower surface: Close to 146A to 146B.

*Peduncles*.—Length: About 2.4 cm. Diameter: About 3 mm. Strength: Strong. Aspect: Upright. Texture and luster: Pubescent; matte. Color: Close to 146B.

*Reproductive organs*.—Stamens: Quantity and arrangement: Four per flower, filaments partially adnate to corolla tube. Filament length: About 1 cm. Filament color: Close to 145C. Anther shape: Round. Anther size: About 1 mm by 1 mm. Anther color: Close to 151A. Pollen amount: Scarce. Pollen color: Close to 151C. Pistils: Quantity: One per flower. Pistil length: About 1.5 cm. Stigma shape: Bi-parted. Stigma diameter: About 1 mm. Stigma color: Close to 146A. Style length: About 1.3 cm. Style color: Close to 145B. Ovary color: Close to 144B. Fruits and seeds: To date, fruit and seed development have not been observed on plants of the new *Verbena*.

Temperature tolerance: Plants of the new *Verbena* have been observed to tolerate temperatures from about 2° C. to about 40° C. and are suitable for USDA Hardiness Zones 8a to 11b.

Pathogen & pest resistance: Plants of the new *Verbena* have been observed to be relatively tolerant to Powdery Mildew (*Podosphaera xanthii*). To date, plants of the new *Verbena* have not been observed to be resistant to pests and other pathogens common to *Verbena* plants.

It is claimed:

1. A new and distinct *Verbena* plant named 'RIKAV44101' as illustrated and described.

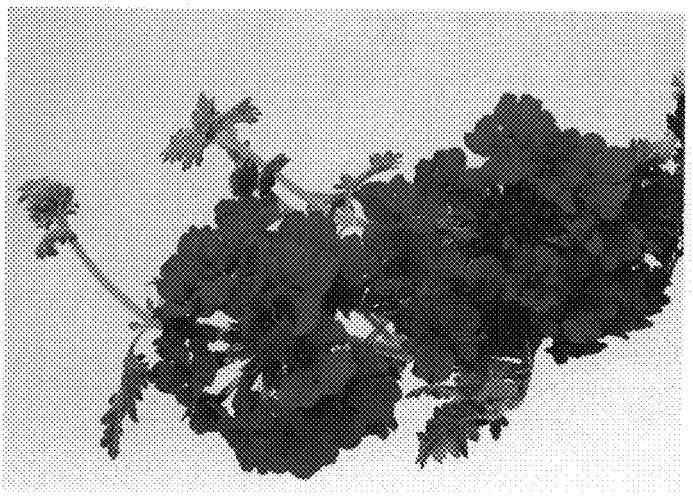
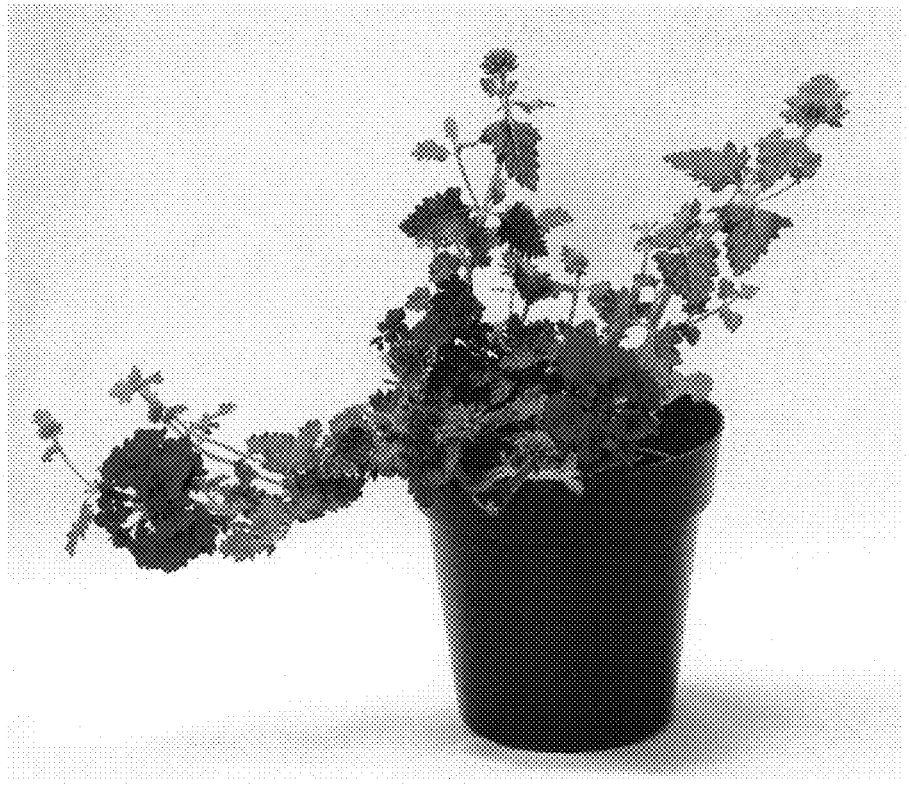

* * * * *